United States Patent [19]

Furukawa et al.

[11] Patent Number: 4,833,242
[45] Date of Patent: May 23, 1989

[54] CEPHALOSPORIN DERIVATIVES AND SALTS THEREOF

[75] Inventors: Minoru Furukawa; Hiroaki Tagawa; Takeshi Hayano; Akio Ejima, all of Tokyo, Japan

[73] Assignee: Daiichi Seiyaku Co., Ltd., Tokyo, Japan

[21] Appl. No.: 724,211

[22] Filed: Apr. 17, 1985

[30] Foreign Application Priority Data

Apr. 17, 1984 [JP] Japan ................................. 59-77182
Jun. 20, 1984 [JP] Japan ................................ 59-126773

[51] Int. Cl.$^4$ ................. C07D 501/38; A61K 31/545
[52] U.S. Cl. .................................... 540/225; 514/203; 514/206
[58] Field of Search ................. 540/225; 514/203, 206

[56] References Cited

U.S. PATENT DOCUMENTS 4,358,448 11/1982 Perrone et al. ..................... 514/203
4,563,449 1/1986 Terajii et al. ...................... 540/225

FOREIGN PATENT DOCUMENTS 0074653 3/1983 European Pat. Off. .
2098216 11/1982 United Kingdom .

Primary Examiner—Nicholas S. Rizzo
Attorney, Agent, or Firm—Sughrue, Mion, Zinn, Macpeak & Seas

[57] ABSTRACT

Novel cephalosporin derivatives and salts thereof are disclosed. These compounds exhibit excellent antimicrobial activity against a wide variety of Gram-negative and Gram-positive bacteria and also have other excellent characteristics as a medicine such as stability and low toxicity. These compounds can be administered in a form of subcutaneous, intravenous or intramuscular injections.

9 Claims, No Drawings

CEPHALOSPORIN DERIVATIVES AND SALTS THEREOF

FIELD OF THE INVENTION

This invention relates to cephalosporin derivatives and salts thereof useful as antimicrobial agents.

BACKGROUND OF THE INVENTION

Hitherto, a wide variety of cephalosporin type antimicrobial agents have been disclosed in a number of publications. Of these known compounds, cephalosporin compounds having 2-(2-aminothiazol-4-yl)-2-methoxyiminoacetamido group at the 7-position and a substituted pyridiniomethyl group at the 3-position of the cephem ring have recently been disclosed, for example, in Japanese Patent Application (OPI) No. 192394/82 (the term "OPI" as used herein refers to a "published unexamined Japanese patent application"). A typical example of this type compound described in the above prior art is 7β-[2-(2-aminothiazol-4-yl)-2-methoxyiminoacetamido]-3-[4-(pyridin-2-yl)-1-pyridinio]methyl-3-cephem-4-carboxylate. However, this known compound is still unsatisfactory as antimicrobial agent.

DETAILED DESCRIPTION OF THE INVENTION

The present invention provides novel cephalosporin derivatives and salts thereof having excellent antimicrobial activity and other excellent characteristics as a medicine such as stability and low toxicity.

The cephalosporin derivatives according to the present invention are represented by the formula (I):

wherein $R_1$ represents an alkyl group, Y represents a 5-membered heterocyclic group and n represents an integer of 0, 1 or 2, and the salts thereof.

The term "alkyl" as used herein for $R_1$ means a straight or branched chain alkyl group having 1 to 4 carbon atoms, for example, methyl, ethyl, n-propyl, isopropyl, n-butyl, tert-butyl, etc.

The term "5-membered heterocyclic group" as used herein includes pyrrolyl, pyrazolyl, imidazolyl, 1,2,3-triazolyl, 1,2,4-triazolyl, thiazolyl, isothiazolyl, 1,2,3-thiadiazolyl, 1,2,4-thiadiazolyl, 1,2,5-thiadiazolyl, 1,3,4-thiadiazolyl, oxazolyl, isoxazolyl, 1,3,4-oxadiazolyl, 1,2,3-oxadiazolyl, 1,2,4-oxadiazolyl, 1,2,5-oxadiazolyl, pyrrolidinyl, 2-pyrrolinyl, 3-pyrrolinyl, 2-imidazolinyl, 3-imidazolinyl, 4-imidazolinyl, 2-oxazolinyl, 3-oxazolinyl, 4-oxazolinyl, 2-thiazolinyl, 3-thiazolinyl, 4-thiazolinyl, 1H-tetrazolyl, 2H-tetrazolyl, oxazolidinyl, isoxazolidinyl, thiazolidinyl, isothiazolidinyl, imidazolidinyl, pyrazolidinyl groups and the like.

The salts of the compounds represented by the formula (I) includes those formed with organic acids such as formic acid, methanesulfonic acid, etc., and inorganic acids such as hydrochloric acid, sulfuric acid, etc., as well as alkali metal or alkaline earth metal salts of carboxylic acid such as sodium salt, potassium salt, magnesium salt, calcium salt and the like.

The compounds of the present invention having the formula (I) can be prepared by the following Process A, B or C.

Process A wherein $R_1$, Y and n are as defined above, and $R_2$ represents an alkyl group having 1 to 4 carbon atoms.

In Process A, the desired compounds of the formula (I) can be prepared by reacting the compound of the formula (II) or a salt thereof with the compound of the formula (III). This reaction can be carried out in water, an aqueous solvent such as a mixture of water and acetonitrile, acetone or dioxane, or a buffer solution of an inorganic salt such as a phosphate buffer solution, in the presence of an inorganic salt such as sodium iodide, potassium thiocyanate and the like or in the presence of an organic salt such as sodium p-toluene-sulfonate and the like. The amount of water or the aqueous solvent is preferably as small volume as possible. The reaction can be carried out at a temperature of from about 40° C. to about 100° C., preferably at 60° C. to 80° C., for a period of from about 15 minutes to about 8 hours, preferably 30 minutes to 4 hours. If necessary, the pH value of the reaction mixture may be adjusted in the range of from 3 to 8 by adding an inorganic acid such as hydrochloric acid. The inorganic or organic salt used in the reaction is preferably sodium iodide or potassium thiocyanate, and can be used in an amount of about 5 to about 30 moles per mole of the compound of the formula (II). The compound of the formula (III) can be used in an amount of from an equimolar amount to about 10 moles per mole of the compound of the formula (II).

Process B

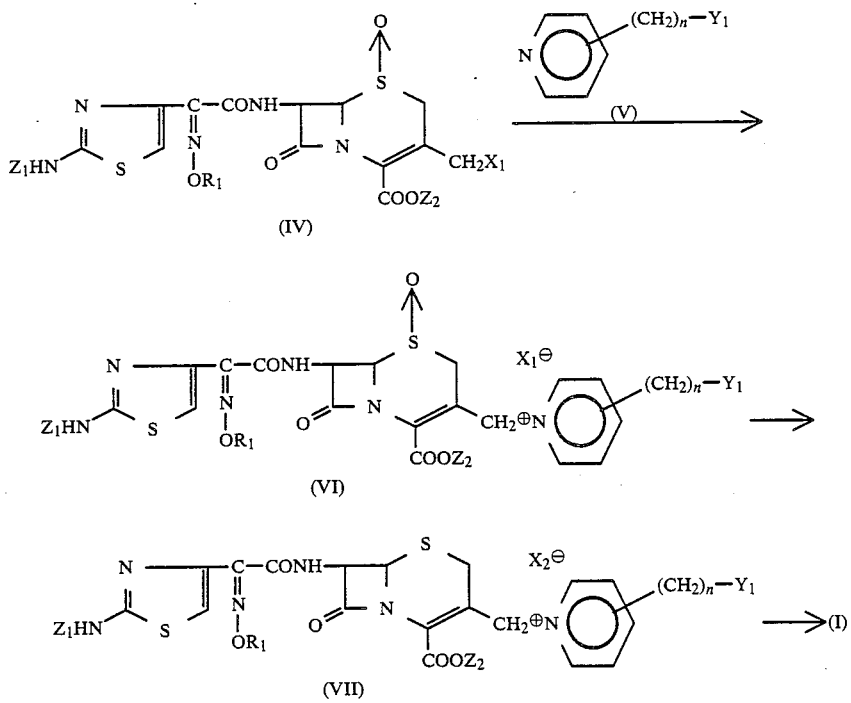

wherein $R_1$ and $n$ are as defined above, $Z_1$ represents a protecting group for an amino group, $Z_2$ represents a protecting group for a carboxyl group, $Y_1$ represents a protected or unprotected group $Y$ wherein $Y$ is as defined above, and $X_1$ and $X_2$ represent halogen atoms which may be the same as or different from each other.

The protecting group for an amino group includes formyl, trityl, tert-butoxycarbonyl and p-methoxybenzyloxycarbonyl groups, etc., and the protecting group for a carboxyl group includes p-nitrobenzyl, tert-butyl and benzhydryl groups, etc.

When the heterocyclic group Y contains one or more of nitrogen atoms as ring hetero atoms and these nitrogen atoms are bonded to hydrogen atoms, the reaction is preferably carried out after these nitrogen atoms are protected with the protecting group for an amino group as exemplified for $Z_1$.

As is apparent from the above reaction scheme, Process B involves substitution reaction, deoxidation reaction and reaction for removing protecting groups, and each of these reactions is hereinafter described in detail.

SUBSTITUTION REACTION

In this reaction, a compound of the formula (IV) is reacted with a compound of the formula (V) in an inert solvent such as acetone, methyl ethyl ketone, dichloromethane, tetrahydrofuran or acetonitrile or a mixture thereof to obtain a compound of the formula (VI). The reaction can be carried out at a temperature of from about 0° to about 50° C., preferably 10° to 30° C., for a period of from about 3 to about 24 hours.

DEOXIDATION REACTION

The compound of the formula (VI) obtained above is reacted with a deoxidizing agent such as phosphorus trichloride or phosphorus tribromide in an inert solvent such as N,N-dimethylformamide or N,N-dimethylacetamide to obtain a compound of the formula (VII). The reaction can be carried out at a temperature of from about −70° C. to about 0° C., preferably −50° to 20° C., for a period of from about 15 minutes to about 3 hours, preferably 30 to 60 minutes.

REACTION FOR REMOVING PROTECTING GROUPS

The reaction for removing protecting groups from the compound of the formula (VII) obtained above can be carried out in an inorganic acid such as hydrochloric acid, or an organic acid such as formic acid or trifluoroacetic acid, or a mixture thereof to obtain the desired compound of the formula (I). Alternatively, this reaction can be carried out in the presence of a scavenger such as anisole or thioanisole. The reaction can be carried out at a temperature of from about 0° to about 50° C., preferably 15° to 30° C., for a period of from about 15 minutes to about 3 hours, preferably from 30 minutes to 2 hours.

Process C

-continued

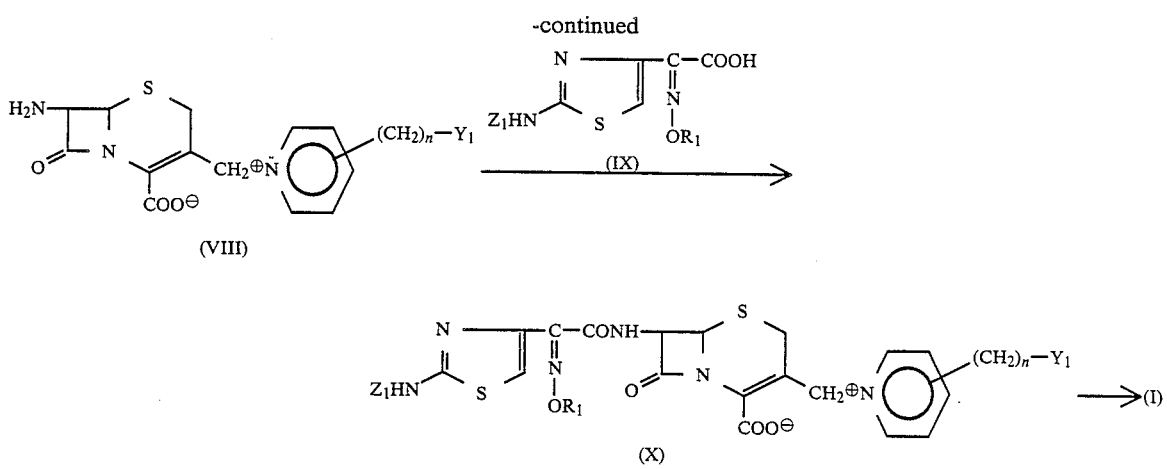

wherein $R_1$, $Y_1$, $Z_1$ and n are as defined above.

As is apparent from the above reaction scheme, this process involves condensation reaction and reaction for removing protecting groups, and each of these reactions is hereinafter described in detail.

CONDENSATION REACTION

The condensation reaction between the compound of the formula (VIII) and the compound of the formula (IX) can be carried out using a reactive derivative of the compound of the formula (IX) in an inert solvent such as ethyl acetate, acetonitrile, dichloromethane, etc., in the presence of N,O-bis(trimethylsilyl)-acetamide, triethylamine, sodium bicarbonate or propylene oxide, etc., to obtain the compound of the formula (X). The reaction can be carried out at a temperature of from about $-50°$ C. to about $50°$ C., preferably from $-20°$ to $30°$ C.

The reactive derivative of the compound of the formula (IX) used in this reaction can be formed by treating a compound of the formula (IX) with phosphorus pentachloride, thionyl chloride, oxalyl chloride or the like, or by treating a compound of the formula (IX) with the Vilsmeier reagent prepared from N,N-dimethylformamide and phosphorus oxychloride, etc.

REACTION FOR REMOVING PROTECTING GROUPS

This reaction can be carried out in the same manner as described in Process B thereby obtaining the desired compound of the formula (I) from the compound of the formula (X).

The compounds represented by the formula (I) according to the present invention and the intermediates therefor have an oxyimino group and, therefore, these compounds exist in the forms of their syn or anti isomer as shown by the following partial structure:

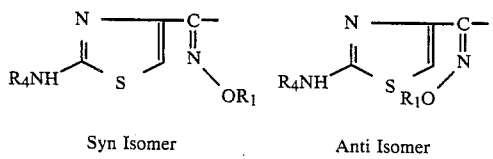

Syn Isomer    Anti Isomer wherein $R_1$ is as defined above and $R_4$ represents a hydrogen atom or an amino-protecting group $Z_1$. Generally, syn isomers exhibit higher antimicrobial activity than do anti isomers.

In the present specification and claims, the syn isomer and the anti isomer are represented by the following partial structure for the sake of convenience:

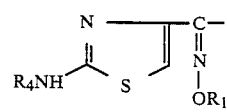

wherein $R_1$ and $R_4$ are as defined above, but the present invention should be understood as including in its scope either of the isomers as well as a mixture thereof.

Further, the compounds of the formula (I) and the intermediates therefor include tautomers with respect to the 2-aminothiazole moiety, which exist in the following equilibrium relation:

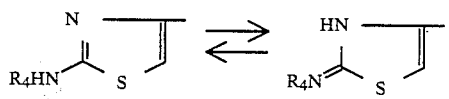

wherein $R_4$ is as defined above. These partial structures are mutually conversible and, therefore, can be considered equivalent to each other. In the present specification and claims, the partial structure is represented by one of the tautomers having the following partial structure for the sake of convenience,

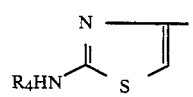

wherein $R_4$ is as defined above, but the present invention is not limited thereto.

The compounds of the formula (I) of the present invention exhibit a broad antibacterial spectrum, and exhibit potent antibacterial activities against a wide variety of Gram-negative bacteria including *Pseudomonas aeruginosa* and Gram-positive bacteria. The antimicrobial activity (MIC) of typical compounds of the present invention are shown in Table below in comparison with Cefotaxime as control.

TABLE

Minimum Inhibitory Concentration (MIC, μg/ml)
(Broth dilution method, inoculated amount: $10^6$ cells/ml, incubated at 37° C. for 18 hours)

| Test Organisms | Compound A | Compound B | Compound C | Compound D | Compound E | Compound F | Compound G | Compound H | Cefotaxime |
|---|---|---|---|---|---|---|---|---|---|
| E. coli, NIHJ | <0.1 | <0.1 | <0.1 | <0.1 | <0.1 | <0.1 | <0.1 | <0.1 | <0.1 |
| Pr. vulgaris, 08601 | <0.1 | <0.1 | <0.1 | <0.1 | <0.1 | 0.1 | 0.1 | <0.1 | <0.1 |
| Ser. marcescens, 10104 | <0.1 | <0.1 | <0.1 | <0.1 | <0.1 | <0.1 | <0.1 | <0.1 | 0.39 |
| Ps. aeruginosa, 32104 | 1.56 | 1.56 | 25.0 | 3.13 | 1.56 | 0.78 | 3.13 | 1.56 | 25.0 |
| Ps. aeruginosa, 32234 | 1.56 | 0.78 | 1.56 | 1.56 | 0.78 | 0.78 | 1.56 | 0.78 | 12.5 |
| Ps. aeruginosa, 32121 | 1.56 | 0.78 | 12.5 | 1.56 | 0.78 | 0.78 | 1.56 | 1.56 | 12.5 |
| Ps. putida, IID 5121 | 1.56 | 6.25 | 12.5 | 3.13 | 3.13 | 1.56 | 12.5 | 12.5 | 50.0 |
| S. aureus, 209P | 0.39 | 0.78 | 0.78 | 0.78 | 0.39 | 0.39 | 0.39 | 0.39 | 3.13 |

Compound A: 7β-[2-(2-Aminothiazol-4-yl)-2-methoxyiminoacetamido]-3-[4-(imidazol-1-yl)-1-pyridinio]-methyl-3-cephem-4-carboxylate trihydrochloride (syn isomer)

Compound B: 7β-[2-(2-Aminothiazol-4-yl)-2-methoxyiminoacetamido]-3-[4-(1,2,4-triazol-1-yl)-1-pyridinio]methyl-3-cephem-4-carboxylate dihydrochloride (syn isomer)

Compound C: 7β-[2-(2-Aminothiazol-4-yl)-2-methoxyiminoacetamido]-3-[4-(imidazol-2-yl)-1-pyridinio]-methyl-3-cephem-4-carboxylate trihydrochloride (syn isomer)

Compound D: 7β-[2-(2-Aminothiazol-4-yl)-2-methoxyiminoacetamido]-3-[4-(oxazol-2-yl)-1-pyridinio]-methyl-3-cephem-4-carboxylate (syn isomer)

Compound E: 7β-[2-(2-Aminothiazol-4-yl)-2-methoxyiminoacetamido]-3-[4-(oxazol-5-yl)-1-pyridinio]-methyl-3-cephem-4-carboxylate (syn isomer)

Compound F: 7β-[2-(2-Aminothiazol-4-yl)-2-methoxyiminoacetamido]-3-[4-(1,3,4-oxadiazol-2-yl)-1-pyridinio]-methyl-3-cephem-4-carboxylate (syn isomer)

Compound G: 7β-[2-(2-Aminothiazol-4-yl)-2-methoxyiminoacetamido]-3-[3-(oxazol-5-yl)-1-pyridinio]-methyl-3-cephem-4-carboxylate (syn isomer)

Compound H: 7β-[2-(2-Aminothiazol-4-yl)-2-methoxyiminoacetamido]-3-[4-(1,2,3-thiadiazol-4-yl)-1-pyridinio]methyl-3-cephem-4-carboxylate dihydrochloride (syn isomer)

Cefotaxime: Sodium 7β-[2-(2-aminothiazol-4-yl)-2-methoxyiminoacetamido]-3-acetoxymethyl-3-cephem-4-carboxylate (syn isomer)

Of the compounds represented by the formula (I), a preferred class of compounds includes those having the formula (I) wherein n is 0 and Y represents an oxazolyl group, an oxadiazolyl group or an imidazolyl group, and more preferred compounds are those having the formula (I) wherein $R_1$ represents a methyl group, n is 0 and Y represents an oxazolyl group.

The cephalosporin derivatives of the formula (I) and the salts thereof according to the present invention can be administered in a form of subcutaneous, intravenous or intramuscular injections at a dosage level of 0.5 to 10 g per day for adult human. The above injections can be prepared by dissolving the compound of the formula (I) in a physiological saline solution or an inorganic salt buffer solution, for example, a phosphate buffer solution. Alternatively, these preparations can be prepared by dissolving a salt of the compound of the formula (I) with a physiologically acceptable inorganic acid such as hydrochloric acid, sulfuric acid, etc., in an inorganic buffer solution such as a phosphate buffer solution and then adjusting the pH of the aqueous solution to a physiologically acceptable pH value with an inorganic salt such as sodium bicarbonate, sodium carbonate, potassium carbonate.

The compounds of this invention are also characterized by low toxicity and, therefore, have a wide safety margin. For example, when the above Compound E is administered intravenously to male rats at various dosage levels of 100, 300 or 1,000 mg/kg for 10 consecutive days, no abnormality were observed in body weight, clinical examinations, weight of various organs and histological findings. Also, the compounds of this invention have been found to not substantially affect on renal functions and morphology in the test using rabbits.

The compounds of this invention exhibit low acute toxicity. For example, $LD_{50}$ value of Compounds D, E and F is more than 4 g/kg (i.v. in mice), and $LD_{50}$ value of Compound A is in the range of from 2 to 4 g/kg (i.v. in mice).

The compounds of this invention have been found to have excellent stability in aqueous solution thereof, especially in a pH of from 4 to 7.5 which is suitable for injections. Also, inorganic slats of the compounds of this invention have been found to have excellent stability in crystal form. These facts have been confirmed by the accelerated deterioration test and stability test. Thus, these compounds are very useful in formulating into various preparations for administration.

The present invention is further illustrated in greater detail by the following examples, but the present invention is not limited thereto.

EXAMPLE 1

7β-[2-(2-Aminothiazol-4-yl)-2-methoxyiminoacetamido]-3-[4-(oxazol-2-yl)-1-pyridinio]methyl-3-cephem-4-carboxylate (syn isomer)

0.75 g of sodium 7β-[2-(2-aminothiazol-4-yl)-2-methoxyiminoacetamido]-3-acetoxymethyl-3-cephem-4-carboxylate (hereinafter referred to Compound 1), 2.25 g of sodium iodide and 0.51 g of 4-(oxazol-2-yl)-pyridine were added to a mixture of 0.4 ml of 4 N hydrochloric acid and 1.2 ml of acetonitrile, followed by stirring at 80° C. for 1 hour. After allowing the mixture to cool, the reaction mixture was poured into acetone, and the precipitate formed was separated by filtration and washed with acetone. The resulting crude powder was dissolved in water, and the solution was subjected to column chromatography of Diaion HP-20 (trade name of Mitsubishi Chemical Industries, Ltd.). The column was developed with a mixture of water-tetrahydrofuran (93:7 by volume). The eluate was further subjected to reversed phase high performance liquid chromatography (column packing: Develosil, trade name of Nomura Chemical Co., Ltd.) and developed with a mixture of water-acetonitrile (89:11 by volume) to obtain the titled compound. Melting point: 160°–170° C. (decomposition).

FT-NMR ($\delta$ in D$_2$O, ppm): 3.13, 3.76 (2H, ABq, cephem ring 2-H); 3.94 (3H, s, methoxy group); 5.31 (1H, d, cephem ring 6-H); 5.36, 5.66 (2H, ABq, cephem ring 3-CH$_2$); 5.84 (1H, d, cephem ring 7-H); 6.98 (1H, s, thiazole ring 5-H); 7.61, 8.26 (each 1H, each s, oxazole ring H); 8.55, 9.14 (each 2H, each d, pyridine ring H).

EXAMPLE 2

7$\beta$-[2-(2-Aminothiazol-4-yl)-2-methoxyiminoacetamido]-3-[4-(oxazol-5-yl)-1-pyridinio]methyl-3-cephem-4-carboxylate (syn isomer)

1.5 g of Compound 1, 4.5 g of sodium iodide and 1.32 g of 4-(oxazol-5-yl)pyridine were added to a mixture of 0.85 ml of 4 N hydrochloric acid and 2.5 ml of acetonitrile, followed by stirring at 80° C. for 70 minutes. The reaction mixture was poured into acetone, and the precipitate formed was separated by filtration and washed with acetone. The resulting powder was subjected to column chromatography of Diaion HP-20 and developed with a mixture of water-tetrahydrofuran (93:7 by volume). Then, the eluate was subjected to reversed phase high performance liquid chromatography (column packing: Develosil) and developed with a mixture of water-acetonitrile (89:11 by volume) to obtain the titled compound.

IR $\nu_{max}^{KBr}$ cm$^{-1}$: 1765.

FT-NMR ($\delta$ in D$_2$O, ppm): 3.17, 3.76 (2H, ABq, J=18 Hz. cephem ring 2-H); 3.91 (3H, s, methoxy group); 5.32 (1H, d, J=5 Hz, cephem ring 6 -H); 5.23, 5.60 (2H, ABq, 4=15 Hz, cephem ring 3-CH$_2$); 5.79 (1H, d, J=5 Hz, cephem ring 7-H); 6.74 (1H, s, thiazole ring 5-H); 8.16 (1H, s, oxazole ring 4-H); 8.55 (1H, s, oxazole ring 2-H); 8.24, 9.02 (each 2H, each d, J=7 Hz, pyridine ring H).

EXAMPLE 3

7$\beta$-[2-(2-Aminothiazol-4-yl)-2-methoxyiminoacetamido]-3-[4-(1,3,4-oxadiazol-2-yl)-1-pyridinio]-methyl-3-cephem-4-carboxylate (syn isomer)

2.0 g of Compound 1 was reacted with 1.76 of 4-(1,3,4-oxadiazol-2-yl)pyridine in the same manner as described in Example 1 to obtain the titled compound.

IR $\nu_{max}^{KBr}$ cm$^{-1}$: 1770.

FT-NMR ($\delta$ in D$_2$O, ppm): 3.21, 3.79 (2H, ABq, J=18 Hz, cephem ring 2-H); 3.94 (3H, s, methoxy group); 5.33 (1H, d, J=5 Hz, cephem ring 6-H); 5.39, 5.76 (2H, ABq, J=14 Hz, cephem ring 3-CH$_2$); 5.81 (1H, d, J=5 Hz, cephem ring 7-H); 6.81 (1H, s, thiazole ring 5-H); 8.69, 9.33 (each 2H, each d, J=7 Hz, pyridine ring H); 9.30 (1H, s, oxadiazole ring H).

EXAMPLE 4

7$\beta$-[2-(2-Aminothiazol-4-yl)-2-methoxyiminoacetamido]-3-[3-(oxazol-5-yl)-1-pyridinio]methyl-3-cephem-4-carboxylate (syn isomer)

2.0 g of Compound 1 was reacted with 1.6 g of 3-(oxazol-5-yl)pyridine in the same manner as described in Example 1 to obtain the titled compound.

IR $\nu_{max}^{KBr}$ cm$^{-1}$: 1765.

FT-MNR ($\delta$ in D$_2$O, ppm): 3.22, 3.74 (2H, ABq, J=18 Hz, cephem ring 2-H); 3.96 (3H, s, methoxy group); 5.31 (1H, d, J=4 Hz, cephem ring 6-H); 5.36, 5.68 (2H, ABq, J=14 Hz, cephem ring 3-CH$_2$); 5.83 (1H, d, J=4 Hz, cephem ring 7-H); 6.85 (1H, s, thiazole ring 5-H); 7.88 (1H, s, oxazole ring 4-H); 8.17 (1H, dd, pyridine ring 5-H); 8.43 (1H, s, oxazole ring 2-H); 8.85, 8.99 (each 1H, each d, pyridine ring 4-H and 6-H); 9.50 (1H, s, pyridine ring 2-H).

EXAMPLE 5

7$\beta$-[2-(2-Aminothiazol-4-yl)-2-methoxyiminoacetamido]-3-[4-(1,2,3-thiadiazol-4-yl)-1-pryifinio]-methyl-3-cephem-4-carboxylate dihydrochloride (syn isomer)

Step 1

1.2 g of 4-acetypyridine, 1.1 g of semicarbazide hydrochloride and 1.4 ml of triethylamine were added to 15 ml of ethanol, followed by stirring overnight. The resulting precipitate was separated by filtration to obtain 1.65 g of 4-acetylpyridine semicarbazone. Melting point: 213°–217° C.

CW-NMR ($\delta$ in DMSO-d$_6$, ppm): 2.19 (3H, s, methyl group); 6.56 (2H, bs, —CONH$_2$); 9.53 (1H, bs, —NH—).

16.8 g of 4-acetylpyridine semicarbazone was added to 47 ml of thionyl chloride under ice-cooling, and, after allowing to warm to room temperature, the mixture was stirred for 1 hour. 200 ml of chloroform was added to the reaction mixture, and the resulting mixture was added dropwise to an aqueous solution of sodium carbonate cooled with ice. The chloroform layer was separated, washed with water, dried and concentrated to obtain 3.4 g of 4-(1,2,3-thiadiazol-4-yl)pyridine. Melting point: 121°–123° C.

CW-NMR ($\delta$ in CDCl$_3$, ppm): 7.7–8.0, 8.6–8.9 (each 2H, eacm m, pyridine ring H); 8.44 (1H, s, thiadiazole ring 5-H).

Step 2

2.0 g of Compound 1 was reacted with 1.95 g of 4-(1,2,3-thiadiazol-4-yl)pyridine in the same manner as described in Example 1 to obtain the titled compound.

IR $\nu_{max}^{KBr}$ cm$^{-1}$: 1770.

FT-NMR ($\delta$ in D$_2$O, ppm): 3.38, 3.79 (2H, ABq, J=18 Hz, cephem ring 2-H); 4.06 (3H, s, methoxy group); 5.36 (1H, d, J=5 Hz, cephem ring 6-H); 5.46, 5.73 (2H, ABq, J=15 Hz, cephem ring 3-CH$_2$); 5.91 (1H, d, J=5 Hz, cephem ring 7-H); 7.15 (1H, s, thiazole ring 5-H); 8.77, 9.15 (each 2H, each d, J=7 Hz, pyridine ring H); 9.96 (1H, s, thiadiazole ring 5-H).

EXAMPLE 6

7β-]2-(2-Aminothiazol-4-yl)-2-methoxyiminoacetamido]-3-[4-(imidazol-1-yl)-1-pyridinio]-methyl-3-cephem-4-carboxylate trihydrochloride (syn isomer)

1.0 g of Compound 1 was reacted with 0.6 g of 4-(imidazol-1-yl)pyridine in the same manner as described in Example 1 to obtain the titled compound. Melting point: 155°–165° C. (decomposition).

FT-NMR (δ in $D_2O$, ppm): 3.35, 3.78 (2H, ABq, cephem ring 2-H); 4.05 (3H, s, methoxy group); 5.33 (1H, d, cephem ring 6-H); 5.46, 5.73 (2H, ABq, cephem ring 3-$CH_2$); 5.88 (1H, d, cephem ring 7-H); 7.14 (1H, s, thiazole ring 5-H); 7.80 (1H, s, imidazole ring 4-H); 8.29 (1H, s, imidazole ring 5-H); 8.51, 9.30 (each 2H, each d, pyridine ring H); 9.74 (1H, s, imidazole ring 2H).

In addition to the titled compound, 7β-[2-(2-aminothiazol-4-yl)-2-methoxyiminoacetamido]-3-[3-(4-pyridyl)-1-imidazolio]methyl-3-cephem-4-carboxylate trihydrochloride (syn isomer) was obtained as a by-product after purification of the product by reversed phase high performance liquid chromatography. Melting point: 155°–165° C. (decomposition).

FT-NMR (δ in $D_2O$, ppm): 3.41, 3.80 (2H, ABq, cephem ring 2-H); 4.07 (3H, s, methoxy group); 5.20, 5.40 (2H, ABq, cephem ring 3-$CH_2$); 5.35 (1H, d, cephem ring 6-H); 5.89 (1H, d, cephem ring 7-H); 7.17 (1H, s, thiazole ring 5-H); 8.01, 8.33 (each 1H, each s, imidazole ring 4-H and 5-H); 8.40, 9.11 (each 2H, each d, pyridine ring H); 9.96 (1H, s, imidazole ring 2-H).

EXAMPLE 7

7β-[2-(2-Aminothiazole-4-yl)-2-methoxyiminoacetamido]-3-[4-(1,2,4-triazol-1-yl)-1-pyridinio]-methyl-3-cephem-4-carboxylate dihydrochloride (syn isomer)

2.0 g of Compound 1 was reacted with 2.0 g of 4-(1,2,4-triazol-1-yl)pyridine in the same manner as described in Example 1 to obtain the titled compound. Melting point: 155°–170° C. (decomposition).

FT-NMR (δ in $D_2O$, ppm): 3.38, 3.80 (2H, ABq, cephem ring 2-H); 4.05 (3H, s, methoxy group); 5.36 (1H, d, cephem ring 6-H); 5.41, 5.79 (2H, ABq, cephem ring 3-$CH_2$); 5.89 (1H, d, cephem ring 7-H); 7.14 (1H, s, thiazole ring 5-H); 8.43 (1H, s, triazole ring 3-H); 8.53, 9.16 (each 2H, each d, pyridine ring H); 9.51 (1H, s, triazole ring 5-H).

EXAMPLE 8

7β-[2-(2-Aminothiazol-4-yl)-2-methoxyiminoacetamido]-3-[4-(imidazol-2-yl)-1-pyridinio]-methyl-3-cephem-4-carboxylate trihydrochloride (syn isomer)

1.5 g of Compound 1 was reacted with 2.18 g of 4-(imidazol-2-yl)pyridine in the same manner as described in Example 1 to obtain the titled compound. Melting point: 165°–175° C. (decomposition).

FT-NMR (δ in $D_2O$, ppm): 3.37, 3.79 (2H, ABq, cephem ring 2-H); 4.37 (3H, s, methoxy group); 5.35 (1H, d, cephem ring 6-H); 5.49, 5.73 (2H, ABq, cephem ring 3-$CH_2$); 7.37 (1H, s, thiazole ring 5-H); 7.85 (2H, s, imidazole ring 4-H and 5-H); 8.57, 9.24 (each 2H, each d, pyridine ring H).

EXAMPLE 9

7β-[2-(2-Aminothiazol-4-yl)-2-methoxyiminoacetamido]-3-[4-(pyrazol-1-yl)-1-pyridinio]methyl-3-cephem-4-carboxylate dihydrochloride (syn isomer)

1.0 g of Compound 1 was reacted with 0.87 g of 4-(pyrazol-1-yl)pyridine in the same manner as described in Example 1 to obtain the titled compound. Melting point: 165°–175° C. (decomposition).

FT-NMR (δ in $D_2O$, ppm): 3.38, 3.78 (2H, ABq, cephem ring 2-H); 4.06 (3H, s, methoxy group); 5.35 (1H, d, cephem ring 6-H); 5.35, 5.67 (2H, ABq, cephem ring 3-$CH_2$); 5.90 (1H, d, cephem ring 7-H); 6.83 (1H, t, pyrazole ring 4-H); 7.15 (1H, s, thiazole ring 5-H); 8.10 (1H, d, pyrazole ring 3-H); 8.35, 8.99 (each 2H, each d, pyridine ring H); 8.60 (1H, d, pyrazole ring 5-H).

EXAMPLE 10

7β-[2-(2-Aminothiazol-4-yl)-2-methoxyiminoacetamido]-3-[4-(2-imidazolin-2-yl)-1-pyridinio]-methyl-3-cephem-4-carboxylate trihydrochloride (syn isomer)

1.5 g of Compound 1, 4.5 g of sodium iodide and 2.2 g of 4-(2-imidazolin-2-yl)pyridine were added to a mixture of 1.3 ml of concentrated hydrochloric acid and 2.7 ml of acetonitrile, followed by stirring at 80° C. for 1.5 hours. After allowing to cool, the reaction mixutre was poured into acetone, and the precipitate formed was separated by filtration and washed with acetone. The resulting crude powder was dissolved in water and, after adjusting to pH 8 with Amberlite LA-2 (OH type), the solution was washed with ethyl acetate. The aqueous layer was separated and adjusted to pH 3.5 with 4 N hydrochloric acid. The precipitate formed was separated by filtration, and the filtrate was subjected to column chromatography of Diaion HP-20. The crude powder obtained by development with a mixture of watertetrahydrofuran (95:5 by volume) was then subjected to reversed phase high performance liquid chromatography and developed with water (pH 2 to 3 adjusted with hydrochloric acid) to obtain the titled compound. Melting point: 160°–170° C. (decomposition).

IR $\nu_{max}^{KBr}$ cm$^{-1}$: 1780.

FT-NMR (δ in $D_2O$, ppm): 3.34, 3.68 (2H, ABq, cephem ring 2-H); 4.06 (3H, s, methoxy group); 4.23 (4H, s, imidazoline ring 4-H and 5-H); 5.33 (1H, d, cephem ring 6-H); 5.53, 5.82 (2H, ABq, cephem ring 3-$CH_2$); 5.89 (1H, d, cephem ring 7-H); 7.15 (1H, s, thiazole ring 5-H); 8.50, 9.35 (each 2H, each d, pyridine ring H).

EXAMPLE 11

7β-[2-(2-Aminothiazol-4-yl)-2-methoxyiminoacetamido]-3-[4-(pyrrolidin-1-yl)methyl-1-pyridinio]-methyl-3-cephem-4-carboxylate (syn isomer)

945 mg of Compound 1 was reacted with 973 mg of 4-(pyrrolidin-1-yl)methylpyridine in the same manner as described in Example 10 to obtain the titled compound. Melting point: 140°–160° C. (decomposition).

FT-NMR (δ in $D_2O$, ppm): 2.18 (4H, m, pyrrolidine ring 3-H and 4-H); 3.36, 3.82 (2H, ABq, cephem ring 2-H); 3.54 (4H, m, pyrrolidine ring 2-H and 5-H); 4.11 (3H, s, methoxy group); 5.36 (1H, d, cephem ring 6-H); 5.46, 5.76 (2H, ABq, cephem ring 3-$CH_2$); 5.92 (1H, d, cephem ring 7-H); 7.20 (1H, s, thiazole ring 5-H); 8.30, 9.16 (each 2H, each d, pyridine ring H).

EXAMPLE 12

7β-[2-(2-Aminothiazol-4-yl)-2-methoxyiminoacetamido]-3-[4-(imidazol-1-yl)methyl-1-pyridinio]methyl-3-cephem-4-carboxylate (syn isomer)

Step 1

5.44 g of imidazole was dissolved in 40 ml of N,N-dimethylformamide, and 4.0 g of 50% sodium hydride was added to the solution under ice-cooling to form a sodium salt. Then, 6.56 g of 4-chloromethylpyridine hydrochloride was added to the mixture, followed by stirring at that temperature for 20 minutes. After stirring at room temperature for additional 30 minutes, the mixture was concentrated to dryness under reduced pressure, and water was added to the residue. The resulting mixture was extracted with chloroform, and the extract was washed with a saturated aqueous sodium chloride solution and dried over sodium sulfate. The solvent was distilled off, and the residue was subjected to silica gel column chromatography to obtain 4.64 g of 4-(imidazol-1-yl)methylpyridine as an oil from the fraction eluted with chloroform-methanol (95:5 by volume).

FT-NMR (δ in CDCl$_3$, ppm): 5.13 (2H, s, pyridine ring 4-CH$_2$); 6.86–7.07 (4H, m, pyridine ring 3,5-H and imidazole ring 3,4-H); 7.50 (1H, s, imidazole ring 2-H); 8.50 (2H, m, pyridine ring 2,6-H).

955 mg of Compound 1 was reacted with 955 mg of 4-(imidazol-1-yl)methylpyridine in the same manner as described in Example 10 to obtain the titled compound.

Melting point: 150°–165° C. (decomposition).

FT-NMR (δ in D$_2$O, ppm): 3.20, 3.67 (2H, ABq, cephem ring 2-H); 3.98 (3H, s, methoxy group); 5.29 (1H, d, cephem ring 6-H); 5.34, 5.57 (2H, ABq, cephem ring 3-CH$_2$); 5.79 (2H, s, pyridine ring 4-CH$_2$); 5.87 (1H, d, cephem ring 7-H); 7.02 (1H, s, thiazole ring 5-H); 7.38, 7.41 (each 1H, each s, imidazole ring 4,5-H); 7.82, 8.96 (each 2H, each d, pyridine ring H); 8.36 (1H, s, imidazole ring 2-H).

EXAMPLE 13

5.0 g of the product obtained in Example 1 was dissolved in 25 ml of water, and 13 ml of 2 N sulfuric acid was added thereto. The mixture was allowed to stand for about 30 minutes and the precipitate formed was separated by filtration to obtain 3.3 g of 7β-[2-(2-aminothiazol-4-yl)-2-methoxyiminoacetamido]-3-[4-(oxazol-2-yl)-1-pyridinio]methyl-3-cephem-4-carboxylate (syn isomer) sulfate as crystals. Melting point: higher than 210° C. (decomposition).

IR $\nu_{max}^{KBr}$ cm$^{-1}$: 1795.

FT-NMR (δ in D$_2$O, ppm): 3.34, 3.76 (2H, ABq, J=18 Hz, cephem ring 2-H); 4.06 (3H, s, methoxy group); 5.34 (1H, d, J=5 Hz, cephem ring 6-H); 5.45, 5.63 (2H, ABq, J=14 Hz, cephem ring 3-CH$_2$); 5.91 (1H, d, J=5 Hz, cephem ring 7-H); 7.15 (1H, s, thiazole ring 5-H); 7.64, 8.28 (each 1H, each s, oxazole ring H); 8.61, 9.14 (each 2H, each d, J=7 Hz, pyridine ring H).

Elementary Analysis for C$_{22}$H$_{19}$N$_7$O$_6$S$_2$.H$_2$SO$_4$.½ H$_2$O: Calc'd: C, 40.74; H, 3.41; N, 15.12; S, 14.83. Found: C, 40.97; H, 3.28; N, 15.41; S, 14.76.

EXAMPLE 14

5.0 g of the product obtained in Example 2 was dissolved in 25 ml of water, and 13 ml of 2 N sulfuric acid was added thereto. The resulting mixture was allowed to stand for about 30 minutes, and the precipitate formed was separated by filtration to obtain 3.2 g of 7β-[2-(2-aminothiazol-4-yl)-2-methoxyiminoacetamido]-3-[4-(ocazol-5-yl)-1-pyridinio]methyl-3-cephem-4-carboxylate (syn isomer) sulfate as crystals. Melting point: higher than 200° C. (decomposition).

IR $\nu_{max}^{KBr}$ cm$^{-1}$: 1785.

FT-NMR (δ in D$_2$O, ppm): 3.50, 3.72 (2H, ABq, J=18 Hz, cephem ring 2-H); 4.05 (3H, s, methoxy group); 5.32 (1H, d, J=5 Hz, cephem ring 6-H); 5.36, 5.60 (2H, ABq, J=14 Hz, cephem ring 3-CH$_2$); 5.89 (1H, d, J=5 Hz, cephem ring 7-H); 7.13 (1H, s, thiazole ring 5-H); 8.20 (1H, s, oxazole ring 4-H); 8.55 (1H, s, oxazole ring 2-H); 8.33, 8.97 (each 2H, each d, J=7 Hz, pyridine ring H).

Elementary Analysis for C$_{22}$H$_{19}$N$_7$O$_6$S$_2$.H$_2$SO$_4$.2H$_2$O: Calc'd: C, 39.11; H, 3.73; N, 14.51; S, 14.24. Found: C, 39.16; H, 3.45; N, 14.53; S, 14.63.

EXAMPLE 15

3.0 g of the product obtained in Example 3 was dissolved in 15 ml of water, and 7.0 ml of 2 N sulfuric acid was added thereto. The resulting mixture was allowed to stand for about 30 minutes, and the precipitate formed was separated by filtration to obtain 2.1 g of 7β-[2-(2-aminothiazol-4-yl)-2-methoxyiminoacetamido]-3-[4-(1,3,4-oxadiazol-2-yl)-1-pyridinio]methyl-3-cemphem-4-carboxylate (syn isomer) sulfate as crystals. Melting point: higher than 180° C. (decomposition).

IR $\nu_{max}^{KBr}$ cm$^{-1}$ 1790.

FT-NMR (δ in D$_2$O, ppm): 3.33, 3.77 (2H, ABq, J=18 Hz, cephem ring 2-H); 4.06 (3H, s, methoxy group); 5.35 (1H, d, J=5 Hz, cephem ring 6-H); 5.49, 5.76 (2H, ABq, J=14 Hz, cephem ring 3-CH$_2$); 5.91 (1H, d, J=5 Hz, cephem ring 7-H); 7.15 (1H, s, thiazole ring 5-H); 8.75, 9.30 (each 2H, each d, J=7 Hz, pyridine ring H); 9.29 (1H, s, oxadiazole ring H).

Elementary Analysis for C$_{22}$H$_{19}$N$_7$O$_6$S$_2$.H$_2$SO$_4$.1.5-H$_2$O: Calc'd: C, 37.79; H, 3.47; N, 16,78; S, 14,41. Found: C, 37.78; H, 3,69; N, 16.76; S, 14.19.

While the invention has been described in detail and with reference to specific embodiments thereof, it will be apparent to one skilled in the art that various changes and modifications can be made therein without departing from the spirit and scope thereof.

What is claimed is:

1. A cephalosporin derivative represented by the formula (I)

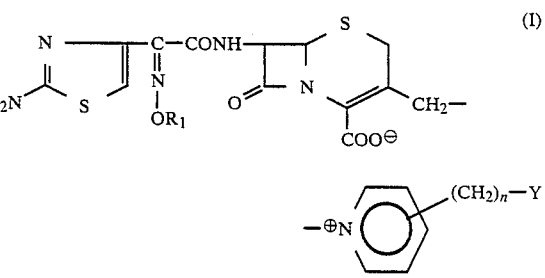

wherein R$_1$ represents an alkyl group having 1 to 4 carbon atoms, Y represents a 5-membered heterocyclic group selected from the group consisting of pyrrolyl, pyrazolyl, imidazolyl, 1,2,3-triazolyl, 1,2,4-triazolyl, thiazolyl, isothiazolyl, 1,2,3-thiadiazolyl, 1,2,4-thiadiazolyl, 1,2,5-thiadiazolyl, 1,3,4-thiadiazolyl, oxazolyl, isoxazolyl, 1,3,4-oxadiazolyl, 1,2,3-oxadiazolyl, 1,2,4-oxadiazolyl, 1,2,5-oxadiazolyl, pyrrolidinyl, 2-pyrrolinyl, 3-pyrrolinyl, 2-imidazolinyl, 3-imidazolinyl, 4-imidazolinyl, 2-oxazolinyl, 3-oxazolinyl, 4-oxazolinyl, 2-thiazolinyl, 3-thiazolinyl, 4-thiazolinyl, 1H-tetrazolyl, 2H-tetrazolyl, oxazolidinyl, isoxazolidinyl, thiazolidinyl, isothiazolidinly, imidazolidinyl and pyrazolidinyl groups and n represents an integer of 0, 1 of 2, and a pharmaceutically acceptable salt thereof.

2. A compound or a salt thereof according to claim 1, wherein n represents 0, and Y represents an oxazolyl group, an oxadiazolyl group or an imidazolyl group.

3. A compound or a salt thereof according to claim 1, wherein n represents 0, Y represents an oxazolyl group and $R_1$ represents a methyl group.

4. 7β-[2-(2-Aminothiazol-4-yl)-2-methoxyiminoacetamido]-3-[4-(oxazol-2-yl)-1-pyridinio]methyl-3-cephem-4-carboxylate or a pharmaceutically acceptable salt thereof according to claim 1.

5. 7β-[2-(2-Aminothiazol-4-yl)-2-methoxyiminoacetamido]-3-[4-(oxazol-5-yl)-1-pyridinio]methyl-3-cephem-4-carboxylate or a pharmaceutically acceptable salt thereof according to claim 1.

6. 7β-[2-(2-Aminothiazol-4-yl)-2-methoxyiminoacetamido]-3-[1-(1,3,4-oxadiazol-2-yl)-1-pyridinio]methyl-3-cephem-4-carboxylate or a pharmaceutically acceptable salt thereof according to claim 1.

7. 7β-[2-(2-Aminothiazol-4-yl)-2-methoxyiminoacetamido]-3-[4-(imidazol-1-yl)-1-pyridinio]-methyl-3-cephem-4-carboxylate or a pharmaceutically acceptable salt thereof according to claim 1.

8. A Cephen compound of formula:

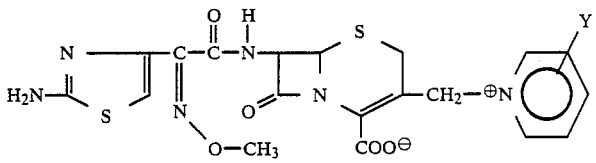

wherein y is an aromatic five membered heterocyclic ring containing 1 to 4 Nitrogen atoms and optionally one oxygen or sulfur which ring is linked to pyridine through a carbon bond and a pharmaceutically acceptable salt thereof.

9. A compound or a pharmaceutically acceptable salt thereof according to claim 1, wherein Y represents imidazolyl, 1,2, 4-triazolyl, 2-imidazolinyl, pyrrolidinyl, pyrazolyl or oxazolyl.

* * * * *